United States Patent

Eckhouse

[11] Patent Number: 5,828,803
[45] Date of Patent: Oct. 27, 1998

[54] SYSTEM FOR PROVIDING PULSED LIGHT TO AN OPTICAL FIBER

[75] Inventor: Shimon Eckhouse, Haifa, Israel

[73] Assignee: ESC Medical Systems, Ltd., Yokneam, Israel

[21] Appl. No.: 398,542

[22] Filed: Mar. 6, 1995

Related U.S. Application Data

[62] Division of Ser. No. 964,210, Oct. 20, 1992, Pat. No. 5,405,368.

[51] Int. Cl.⁶ .................................. G02B 6/36; F21V 7/04
[52] U.S. Cl. .................................. 385/88; 385/43; 362/32; 362/298; 606/16
[58] Field of Search .................................. 385/31, 32, 88, 385/33, 35, 43, 123, 89, 92, 94; 362/32, 298, 261, 297; 606/3, 9, 15–16

[56] References Cited

U.S. PATENT DOCUMENTS

| | | | |
|---|---|---|---|
| 4,022,534 | 5/1977 | Kishner | 356/446 |
| 4,241,382 | 12/1980 | Daniel | 362/32 |
| 4,298,005 | 11/1981 | Mutzhas | 607/94 |
| 4,754,381 | 6/1988 | Downs | 362/292 |
| 4,757,431 | 7/1988 | Cross et al. | 362/261 |
| 4,784,135 | 11/1988 | Blum et al. | 606/3 |
| 4,829,262 | 5/1989 | Furumoto | 359/346 |
| 4,883,333 | 11/1989 | Yanez | 385/33 |
| 4,897,771 | 1/1990 | Parker | 362/298 |
| 4,930,504 | 6/1990 | Diamantopoulos et al. | 606/3 |
| 4,947,305 | 8/1990 | Gunter, Jr. | 362/297 |
| 4,950,880 | 8/1990 | Hayner | 250/201.9 |
| 5,109,463 | 4/1992 | Lee | 385/123 |
| 5,161,526 | 11/1992 | Hellwing et al. | 606/3 |
| 5,207,671 | 5/1993 | Franken et al. | 606/9 |
| 5,217,455 | 6/1993 | Tan | 606/9 |
| 5,259,380 | 11/1993 | Mendes et al. | 606/2 |
| 5,344,418 | 9/1994 | Ghaffari | 606/9 |
| 5,394,307 | 2/1995 | Matsuura | 362/16 |
| 5,414,600 | 5/1995 | Strobl et al. | 362/32 |
| 5,560,699 | 10/1996 | Davenport et al. | 362/32 |

FOREIGN PATENT DOCUMENTS

3906860A1 of 0000 Germany .

*Primary Examiner*—Hemang Sanghavi
*Attorney, Agent, or Firm*—Foley & Lardner

[57] ABSTRACT

A therapeutic treatment device is disclosed and includes a housing and an incoherent light source such as a flashlamp disposed in the housing. The flashlamp provides a pulsed light output for treatment of external skin disorders. To provide light to the treatment area the housing has an opening that is disposed adjacent a skin treatment area. A reflector is mounted within the housing near proximate the light source to reflect the light to the treatment area. At least one optical filter and an iris are mounted near the opening in the housing. Power to the lamp is provided by a pulse forming circuit that can provide a variable pulse width.

4 Claims, 6 Drawing Sheets

SYSTEM FOR PROVIDING PULSED LIGHT TO AN OPTICAL FIBER

This is a divisional of U.S. Ser. No. 07/964,210 filed on Oct. 20, 1992, entitled: METHOD AND APPARATUS FOR THERAPEUTIC ELECTROMAGNETIC now U.S. Pat. No. 5,405,368.

FIELD OF THE INVENTION

The present invention relates generally to the art of therapeutic electromagnetic treatment and more specifically to a method and apparatus for utilizing a spatially extended pulsed light source such as a flashlamp (flash tube) for such a treatment or, efficiently focusing light from the flashlamp into optical fibers for therapeutic treatment or other applications.

BACKGROUND OF THE INVENTION

It is known in the prior art to use electromagnetic radiation in medical application for therapeutic uses such as treatment of skin disorders. For example, U.S. Pat. No. 4,298,005 to Mutzhas describes a continuous ultraviolet lamp with cosmetic, photobiological, and photochemical applications. A treatment based on using the UV portion of the spectrum and its photochemical interaction with the skin is described. The power delivered to the skin using Mutzhas' lamp is described as 150 $W/m^2$, which does not have a significant effect on skin temperature.

In addition to prior art treatment involving UV light, lasers have been used for dermatological procedures, including Argon lasers, $CO_2$ lasers, Nd(Yag) lasers, Copper vapor lasers, ruby lasers and dye lasers. For example, U.S. Pat. No. 4,829,262 to Furumoto, describes a method of constructing a dye laser used in dermatology applications. Two skin conditions which may be treated by laser radiation are external skin irregularities such as local differences in the pigmentation or structure of the skin, and vascular disorders lying deeper under the skin which cause a variety of skin abnormalities including port wine stains, telangiectasias, leg veins and cherry and spider angiomas. Laser treatment of these skin disorders generally includes localized heating of the treatment area by absorption of laser radiation. Heating the skin changes or corrects the skin disorder and causes the full or partial disappearance of the skin abnormality.

Certain external disorders such as pigmented lesions can also be treated by heating the skin very fast to a high enough temperature to evaporate parts of the skin. Deeper-lying vascular disorders are more typically treated by heating the blood to a high enough temperature to cause it to coagulate. The disorder will then eventually disappear. To control the treatment depth a pulsed radiation source is often used. The depth the heat penetrates in the blood vessel is controlled by controlling the pulse width of the radiation source. The absorption and scattering coefficients of the skin also affect the heat penetration. These coefficients are a function of the constituents of skin and the wavelength of the radiation. Specifically, the absorption coefficient of light in the epidermis and dermis tends to be a slowly varying, monotonically decreasing function of wavelength. Thus, the wavelength of the light should be chosen so that the absorption coefficient is optimized for the particular skin condition and vessel size being treated.

The effectiveness of lasers for applications such as tattoo removal and removal of birth and age marks is diminished because lasers are monochromatic. A laser of a given wavelength may be effectively used to treat a first type of skin pigmentation disorder, but, if the specific wavelength of the laser is not absorbed efficiently by skin having a second type of disorder, it will be ineffective for the second type of skin disorder. Also, lasers are usually complicated, expensive to manufacture, large for the amount of power delivered, unreliable and difficult to maintain.

The wavelength of the light also affects vascular disorder treatment because blood content in the vicinity of the vascular disorders varies, and blood content affects the absorption coefficient of the treatment area. Oxyhemoglobin is the main chromophore which controls the optical properties of blood and has strong absorption bands in the visible region. More particularly, the strongest absorption peak of oxyhemoglobin occurs at 418 nm and has a band-width of 60 nm. Two additional absorption peaks with lower absorption coefficients occur at 542 and 577 nm. The total band-width of these two peaks is on the order of 100 nm. Additionally, light in the wavelength range of 500 to 600 nm is desirable for the treatment of blood vessel disorders of the skin since it is absorbed by the blood and penetrates through the skin. Longer wavelengths up to 1000 nm are also effective since they can penetrate deeper into the skin, heat the surrounding tissue and, if the pulse-width is long enough, contribute to heating the blood vessel by thermal conductivity. Also, longer wavelengths are effective for treatment of larger diameter vessels because the lower absorption coefficient is compensated for by the longer path of light in the vessel.

Accordingly, a wide band electromagnetic radiation source that covers the near UV and the visible portion of the spectrum would be desirable for treatment of external skin and vascular disorders. The overall range of wavelengths of the light source should be sufficient to optimize treatment for any of a number of applications. Such a therapeutic electromagnetic radiation device should also be capable of providing an optimal wavelength range within the overall range for the specific disorder being treated. The intensity of the light should be sufficient to cause the required thermal effect by raising the temperature of the treatment area to the required temperature. Also, the pulse-width should be variable over a wide enough range so as to achieve the optimal penetration depth for each application. Therefore, it is desirable to provide a light source having a wide range of wavelengths, which can be selected according to the required skin treatment, with a controlled pulse-width and a high enough energy density for application to the affected area.

Pulsed non-laser type light sources such as linear flashlamps provide these benefits. The intensity of the emitted light can be made high enough to achieve the required thermal effects. The pulse-width can be varied over a wide range so that control of thermal depth penetration can be accomplished. The typical spectrum covers the visible and ultraviolet range and the optical bands most effective for specific applications can be selected, or enhanced using fluorescent materials. Moreover, non-laser type light sources such as flashlamps are much simpler and easier to manufacture than lasers, are significantly less expensive for the same output power and have the potential of being more efficient and more reliable. They have a wide spectral range that can be optimized for a variety of specific skin treatment applications. These sources also have a pulse length that can be varied over a wide range which is critical for the different types of skin treatments.

In addition to being used for treating skin disorders, lasers have been used for invasive medical procedures such as lithotripsy and removal of blood vessel blockage. In such invasive procedures laser light is coupled to optical fibers and delivered through the fiber to the treatment area. In lithotripsy the fiber delivers light from a pulsed laser to a kidney or gallstone and the light interaction with the stone creates a shock wave which pulverizes the stone. To remove blood vessel blockage the light is coupled to the blockage by the fiber and disintegrates the blockage. In either case the shortcomings of lasers discussed above with respect to laser skin treatment are present. Accordingly, a treatment device for lithotripsy and blockage removal utilizing a flashlamp would be desirable.

To effectively treat an area the light from the source must be focussed on the treatment area. Coupling pulsed laser light into optical fibers in medicine is quite common. The prior art describes coupling isotropic incoherent point sources such as CW lamps into small optical fibers. For example, U.S. Pat. No. 4,757,431, issued Jul. 12, 1988, to Cross, et al. discloses a method for focusing incoherent point sources with small filaments or an arc lamp with an electrode separation of 2 mm into a small area. Point (or small) sources are relatively easy to focus without large losses in energy because of the small size of the source. Also, U.S. Pat. No. 4,022,534, issued May 10, 1977, to Kishner discloses light produced by a flash tube and the collection of only a small portion of the light emitted by the tube into an optical fiber.

However, the large dimension of an extended source such as a flashlamp make it difficult to focus large fractions of its energy into small areas. Coupling into optical fibers is even more difficult since not only must a high energy density be achieved, but the angular distribution of the light has to be such that trapping in the optical fiber can be accomplished. Thus, it is desirable to have a system for coupling the output of a high intensity, extended, pulsed light source into an optical fiber.

SUMMARY OF THE PRESENT INVENTION

According to a first embodiment of the invention a therapeutic treatment device comprises a housing and an incoherent light source, suitably a flashlamp, operable to provide a pulsed light output for treatment, disposed in the housing. The housing has an opening and is suitable for being disposed adjacent a skin treatment area. A reflector is mounted within the housing proximate the light source, and at least one optical filter is mounted proximate the opening in the housing. An iris is mounted coextensively with the opening. Power to the lamp is provided by a variable pulse width pulse forming circuit. Thus, the treatment device provides controlled density, filtered, pulsed light output through an opening in the housing to a skin area for treatment.

According to a second embodiment of the invention a method of treatment with light energy comprises the steps of providing a high power, pulsed light output from a non-laser, incoherent light source and directing the pulsed light output to a treatment area. The pulse width of the light output is controlled and focussed so that the power density of the light is controlled. Also, the light is filtered to control the spectrum of the light.

According to a third embodiment of the invention a coupler comprises an incoherent light source such as a toroidal flashlamp. A reflector is disposed around the incoherent light source and at least one optical fiber or light guide. The fiber has an end disposed within the reflector. This end collects the light from the circular lamp. In a similar coupling configuration fibers may be provided, along with a linear to circular fiber transfer unit disposed to receive light from the light source and provide light to the optical fibers. The reflector has an elliptical cross-section in a plane parallel to the axis of the linear flash tube, and the linear flash tube is located at one focus of the ellipse while the linear to circular transfer unit is located at the other focus of the ellipse.

BRIEF DESCRIPTION OF THE DRAWINGS

For a better understanding of the invention, reference is made to the accompanying drawings, in which like numerals designate corresponding elements or sections throughout, and in which.

In the various figures, like reference numerals are used to describe like components.

DETAILED DESCRIPTION OF THE PREFERRED EMBODIMENTS

Figure 1:
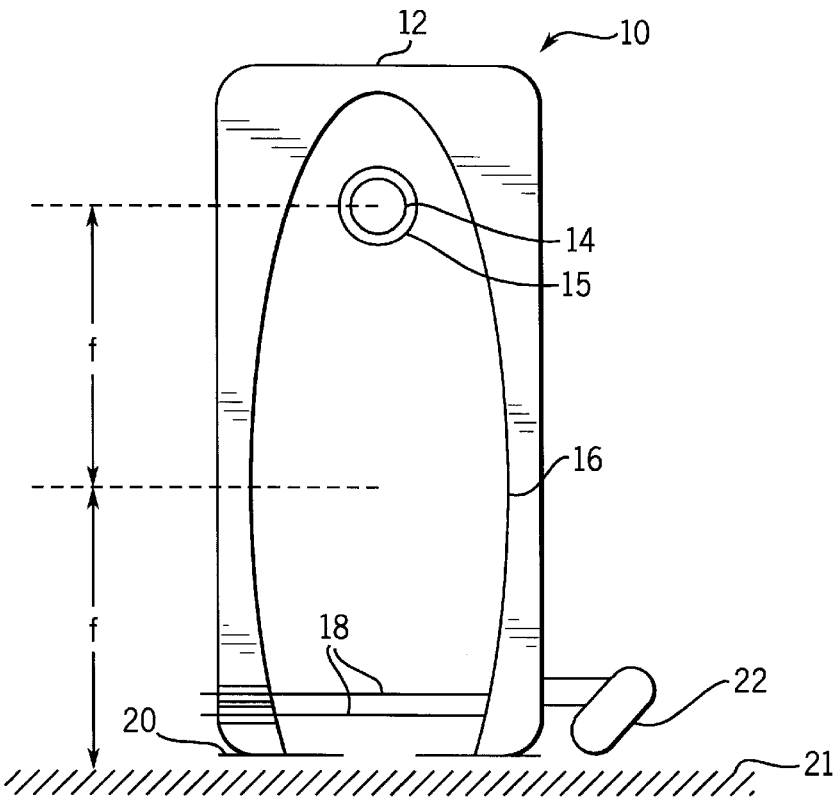
FIG. 1 is a cross-sectional view of an incoherent, pulsed light source skin treatment device.

Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
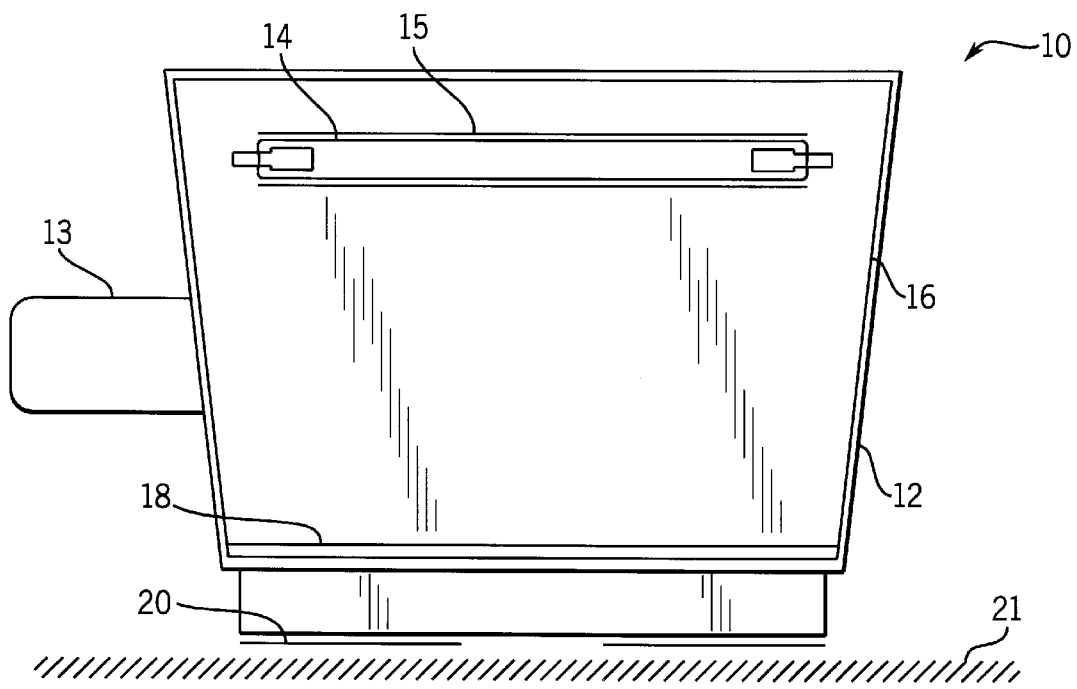
FIG. 2 is a side view of the light source of FIG. 1.

Referring now to FIGS. 1 and 2, cross-sectional and side views of an incoherent, pulsed light source skin treatment device 10 constructed and operated in accordance with the principles of the present invention are shown. The device 10 may be seen to include a housing 12, having an opening therein, a handle 13 (FIG. 2 only), a light source 14 having an outer glass tube 15, an elliptical reflector 16, a set of optical filters 18, an iris 20 and a detector 22 (FIG. 1 only).

Light source 14, which is mounted in housing 12, may be a typical incoherent light source such as a gas filled linear flashlamp Model No. L5568 available from ILC. The spectrum of light emitted by gas filled linear flashlamp 14 depends on current density, type of glass envelope material and gas mixture used in the tube. For large current densities (e.g., 3000 A/Cm² or more) the spectrum is similar to a black body radiation spectrum. Typically, most of the energy is emitted in the 300 to 1000 nm wavelength range.

To treat a skin (or visible) disorder a required light density on the skin must be delivered. This light density can be achieved with the focusing arrangement shown in FIGS. 1 and 2. FIG. 1 shows a cross-section view of reflector 16, also mounted in housing 12. As shown in FIG. 1, the cross-section of reflector 16 in a plane is perpendicular to the axis of flashlamp 14 is an ellipse. Linear flashlamp 14 is located at one focus of the ellipse and reflector 16 is positioned in such a way that the treatment area of skin 21 is located at the other focus. The arrangement shown is similar to focusing arrangements used with lasers and efficiently couples light from flashlamp 14 to the skin. This arrangement should not, however, be considered limiting. Elliptical reflector 16 may be a metallic reflector, typically polished aluminum which is an easily machinable reflector and has a very high reflectivity in the visible, and the UV range of the spectrum can be used. Other bare or coated metals can also be used for this purpose.

Optical and neutral density filters 18 are mounted in housing 12 near the treatment area and may be moved into the beam or out of the beam to control the spectrum and intensity of the light. Typically, 50 to 100 nm bandwidth filters, as well as low cutoff filters in the visible and ultraviolet portions of the spectrum, are used. In some procedures it is desirable to use most of the spectrum, with only the UV portion being cut off. In other applications, mainly for deeper penetration, it is preferable to use narrower bandwidths. The bandwidth filters and the cutoff filters are readily available commercially.

Glass tube 15 is located coaxially with flashlamp 14 and has fluorescent material deposited on it. Glass tube 15 will typically be used for treatment of coagulation of blood vessels to optimize the energy efficiency of device 10. The fluorescent material can be chosen to absorb the UV portion of the spectrum of flashlamp 14 and generate light in the 500 to 650 nm range that is optimized for absorption in the blood. Similar materials are coated on the inner walls of commercial fluorescent lamps. A typical material used to generate "warm" white light in fluorescent lamps has a conversion efficiency of 80%, has a peak emission wavelength of 570 nm and has a bandwidth of 70 nm and is useful for absorption in blood. The few millisecond decay time of these phosphors is consistent with long pulses that are required for the treatment of blood vessels.

Other shapes or configurations of flashlamp 14 such as circular, helical, short arc and multiple linear flashlamps may be used. Reflector 16 may have other designs such as parabolic or circular reflectors. The light source can also be used without a reflector and the required energy and power density may be achieved by locating light source 14 in close proximity to the treatment area.

Iris 20 is mounted in housing 12 between optical filters 18 and the treatment area and controls the length and the width of the exposed area, i.e. by collimating the output of flashlamp 14. The length of flashlamp 14 controls the maximum length that can be exposed. Typically a 8 cm long (arc length) tube will be used and only the central 5 cm of the tube is exposed. Using the central 5 cm assures a high degree of uniformity of energy density in the exposed skin area. Thus, in this embodiment the iris 20 (also called a collimator) will enable exposure of skin areas of a maximum length of 5 cm. The iris 20 may be closed to provide a minimum exposure length of one millimeter. Similarly, the width of the exposed skin area can be controlled in the range of 1 to 5 mm for a 5 mm wide flashlamp. Larger exposed areas can be easily achieved by using longer flash tubes or multiple tubes, and smaller exposure areas are obtainable with an iris that more completely collimates the beam. The present invention provides a larger exposure area compared to prior art lasers or point sources and is very effective in the coagulation of blood vessels since blood flow interruption over a longer section of the vessel is more effective in coagulating it. The larger area exposed simultaneously also reduces the required procedure time.

Detector 22 (FIG. 1) is mounted outside housing 12 and monitors the light reflected from the skin. Detector 22 combined with optical filters 18 and neutral density filters can be used to achieve a quick estimate of the spectral reflection and absorption coefficients of the skin. This may be carried out at a low energy density level prior to the application of the main treatment pulse. Measurement of the optical properties of the skin prior to the application of the main pulse is useful to determine optimal treatment conditions. As stated above, the wide spectrum of the light emitted from the non-laser type source enables investigation of the skin over a wide spectral range and choice of optimal treatment wavelengths.

In an alternative embodiment, detector 22 or a second detector system may be used for real-time temperature measurement of the skin during its exposure to the pulsed light source. This is useful for skin thermolysis applications with long pulses in which light is absorbed in the epidermis and dermis. When the external portion of the epidermis reaches too high a temperature, permanent scarring of the skin may result. Thus, the temperature of the skin should be measured. This can be realized using infra-red emission of the heated skin, to prevent over-exposure.

A typical real-time detector system would measure the infra-red emission of the skin at two specific wavelengths by using two detectors and filters. The ratio between the signals of the two detectors can be used to estimate the instantaneous skin temperature. The operation of the pulsed light source can be stopped if a preselected skin temperature is reached. This measurement is relatively easy since the temperature threshold for pulsed heating that may cause skin scarring is on the order of 50° C. or more, which is easily measurable using infra-red emission.

The depth of heat penetration depends on the light absorption and scattering in the different layers of the skin and the thermal properties of the skin. Another important parameter is pulse-width. For a pulsed light source, the energy of which is absorbed in an infinitesimally thin layer, the depth of heat penetration (d) by thermal conductivity during the pulse can be written as shown in Equation 1:

$$d = 4\,[k\Delta t/C\rho]^{1/2} \qquad \text{(Eq. 1)}$$

where k=heat conductivity of the material being illuminated;

$\Delta t$=the pulse-width of the light pulse;

C=the heat capacity of the material;

$\rho$=density of the material.

It is clear from Equation 1 that the depth of heat penetration can be controlled by the pulse-width of the light source. Thus, a variation of pulse-width in the range of $10^{-5}$ sec to $10^{-1}$ sec will result in a variation in the thermal penetration by a factor of 100.

Accordingly, the flashlamp 14 provides a pulse width of from $10^{-5}$ sec to $10^{-1}$ sec. For treatment of vascular disorders in which coagulation of blood vessels in the skin is the objective the pulse length is chosen to uniformly heat as much of the entire thickness of the vessel as possible to achieve efficient coagulation. Typical blood vessels that need to be treated in the skin have thicknesses in the range of 0.5 mm. Thus, the optimal pulse-width, taking into account the thermal properties of blood, is on the order of 100 msec. If shorter pulses are used, heat will still be conducted through the blood to cause coagulation, however, the instantaneous temperature of part of the blood in the vessel and surrounding tissue will be higher than the temperature required for coagulation and may cause unwanted damage.

For treatment of external skin disorders in which evaporation of the skin is the objective, a very short pulse-width is used to provide for very shallow thermal penetration of the skin. For example, a $10^{-5}$ sec pulse will penetrate (by thermal conductivity) a depth of the order of only 5 microns into the skin. Thus, only a thin layer of skin is heated, and a very high, instantaneous temperature is obtained so that the external mark on the skin is evaporated.

Figure 3:
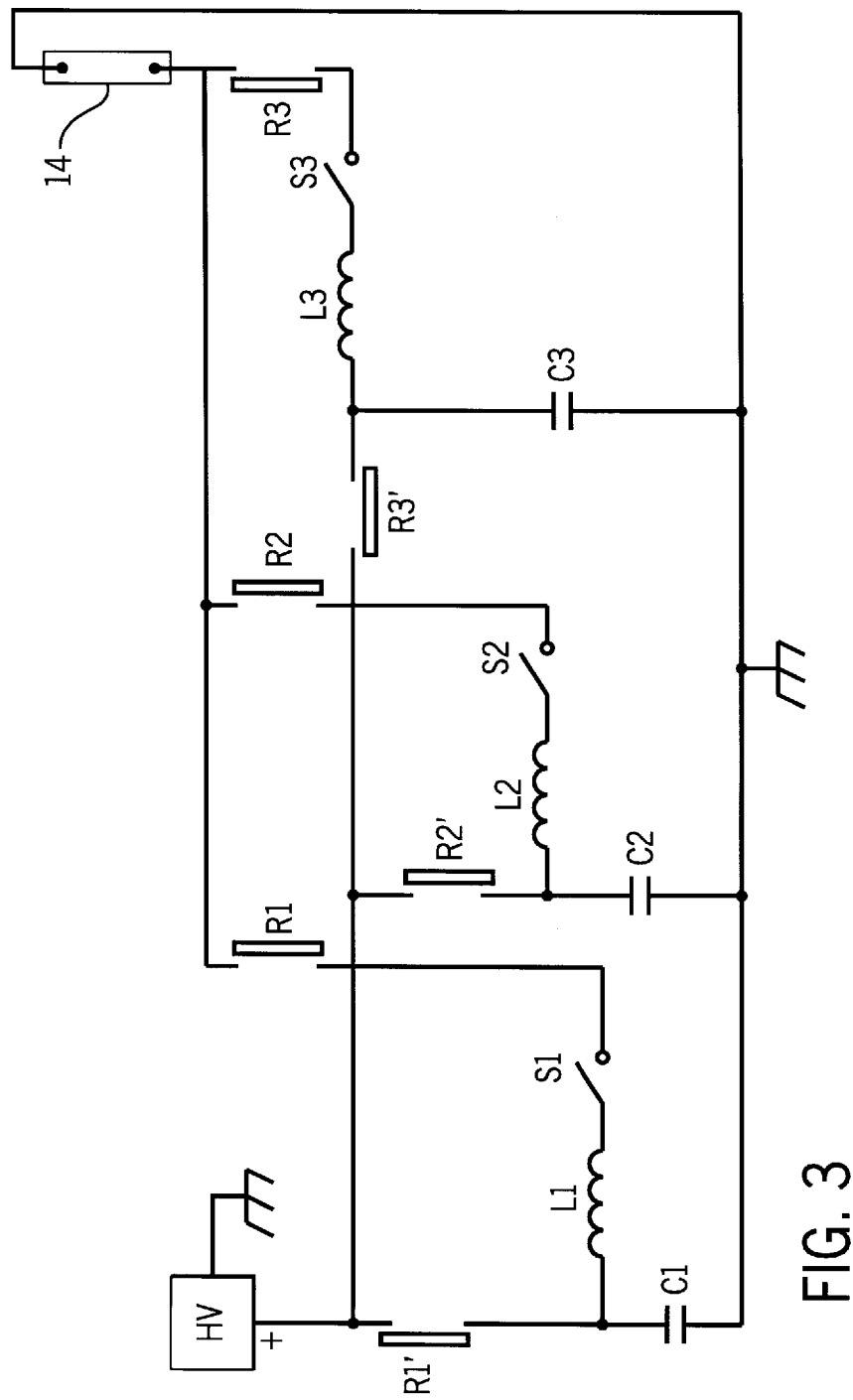
FIG. 3 is a schematic diagram of a pulse forming network with a variable pulse width for use with the skin treatment device of FIGS. 1 and 2.

FIG. 3 shows a variable pulse-width pulse forming circuit comprised of a plurality of individual pulse forming networks (PFN's) that create the variation in pulse-widths of flashlamp 14. The light pulse full width at half maximum (FWHM) of a flashlamp driven by a single element PFN with capacitance C and inductance L is approximately equal to:

$$\Delta t \approx 2[LC]^{1/2} \quad \text{(Eq. 2)}$$

Flashlamp 14 may be driven by three different PFN's, as shown in FIG. 3. The relay contacts R1', R2' and R3' are used to select among three capacitors C1, C2 and C3 that are charged by the high voltage power supply. Relays R1, R2 and R3 are used to select the PFN that will be connected to flashlamp 14. The high voltage switches S1, S2 and S3 are used to discharge the energy stored in the capacitor of the PFN into flashlamp 14. In one embodiment L1, L2 and L3 have values of 100 mH, 1 mH and 5 mH, respectively, and C1, C2 and C3 have values of 100 mF, 1 mF and 10 mF, respectively.

In addition to the possibility of firing each PFN separately, which generates the basic variability in pulse-width, additional variation can be achieved by firing PFN's sequentially. If, for example, two PFN's having pulse-width $\Delta t1$ and $\Delta t2$ are fired, so that the second PFN is fired after the first pulse has decayed to half of its amplitude, then an effective light pulse-width of this operation of the system will be given by the relation: $\Delta t \approx \Delta t1 + \Delta t2$.

The charging power supply typically has a voltage range of 500V to 5 kV. The relays should therefore be high voltage relays that can isolate these voltages reliably. The switches S are capable of carrying the current of flashlamp 14 and to isolate the reverse high voltage generated if the PFNs are sequentially fired. Solid-state switches, vacuum switches or gas switches can be used for this purpose.

A simmer power supply (not shown in FIG. 3) may be used to keep the flashlamp in a low current conducting mode. Other configurations can be used to achieve pulse-width variation, such as the use of a single PFN and a crowbar switch, or use of a switch with closing and opening capabilities.

Typically, for operation of flashlamp 14 with an electrical pulse-width of 1 to 10 msec, a linear electrical energy density input of 100 to 300 J/cm can be used. An energy density of 30 to 100 $J/cm^2$ can be achieved on the skin for a typical flashlamp bore diameter of 5 mm. The use of a 500 to 650 nm bandwidth transmits 20% of the incident energy. Thus, energy densities on the skin of 6 to 20 $J/cm^2$ are achieved. The incorporation of the fluorescent material will further extend the output radiation in the desired range, enabling the same exposure of the skin with a lower energy input into flashlamp 14.

Pulsed laser skin treatment shows that energy densities in the range of 0.5 to 10 $J/cm^2$ with pulse-widths in the range of 0.5 msec are generally effective for treating vascular related skin disorders. This range of parameters falls in the range of operation of pulsed non-laser type light sources such as the linear flashlamp. A few steps of neutral density glass filters 18 can also be used to control the energy density on the skin.

For external disorders a typical pulse-width of 5 microsecond is used. A 20 J/cm electrical energy density input into a 5 mm bore flashlamp results in an energy density on the skin of 10 $J/cm^2$. Cutting off the hard UV portion of the spectrum results in 90% energy transmission, or skin exposure to an energy density of close to 10 $J/cm^2$. This energy density is high enough to evaporate external marks on the skin.

Device 10 can be provided as two units: a lightweight unit held by a physician using handle 13, with the hand-held unit containing flashlamp 14, filters 18 and iris 20 that together control the spectrum and the size of the exposed area and the detectors that measure the reflectivity and the instantaneous skin temperature. The power supply, the PFN's and the electrical controls are contained in a separate box (not shown) that is connected to the hand-held unit via a flexible cable. This enables ease of operation and easy access to the areas of the skin that need to be treated.

The invention has thus far been described in conjunction with skin treatment. However, using a flashlamp rather than a laser in invasive treatments provides advantages as well. Procedures such as lithotripsy or removal of blood vessel blockage may be performed with a flashlamp. Such a device may be similar to that shown in FIGS. 1 and 2, and may use the electronics of FIG. 3 to produce the flash. However, to properly couple the light to an optical fiber a number of couplers 40, 80 and 90 are shown in FIGS. 4 and 8–10, respectively.

Coupler 40 includes an optical source of high intensity incoherent and isotropic pulsed light such as a linear flash tube 42, a light reflector 44 which delivers the light energy to an optical fiber 46. The latter has a generally conical edge in the embodiment of FIG. 4. Optical fiber 46 transfers the light from light collection system 44 to the treatment area. In general, coupler 40 couples pulsed light from a flash tube into an optical fiber and has applications in medical, industrial and domestic areas.

For example, coupler 40 may be used in material processing to rapidly heat or ablate a portion of a material being processed, or to induce a photo-chemical process. Alternatively, coupler 40 may be used in a photography application to provide a flash for picture taking. Using such a coupler would allow the flash bulb to be located inside the camera, with the light transmitted to outside the camera using an optical fiber. As one skilled in the art should recognize coupler 40 allows the use of incoherent light in many applications that coherent or incoherent light has been used in the past.

Figure 5:
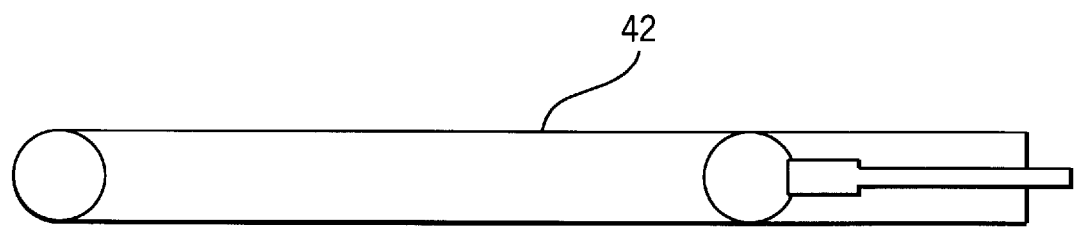
FIG. 5 is a side view of a toroidal flash tube.
Figure 6:
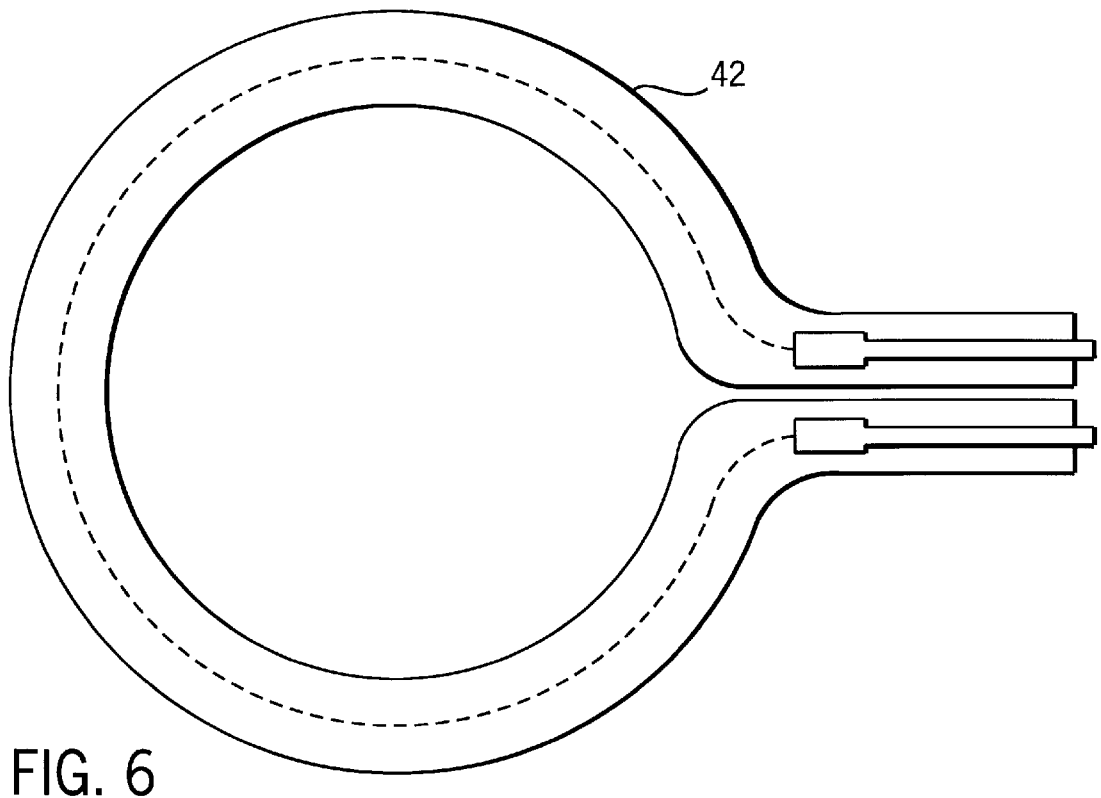
FIG. 6 is a top view of a toroidal flash tube.

To provide for coupling the light to an optical fiber, flash tube 42 has a toroidal shape, shown in FIGS. 5 and 6, and is disposed inside reflector 44. In addition to the toroidal shape other shapes, such as a continuous helix, may be used for flash tube 42. However, a helical tube is more difficult to manufacture than a toroidal tube. Referring now to FIG. 6, flash tube 42 is generally in the shape of a torus, but is not a perfect tours since the electrodes located at the end of the tours have to be connected to the power source. This does not create a significant disturbance in the circular shape of flash tube 42, since the connection to the electrodes can be made quite small.

Reflector 44 collects and concentrates the light, and has a cross-section of substantially an ellipse, in a plane perpendicular to the minor axis of the toroidal flash tube 42. The major axis of this ellipse preferably forms a small angle with the major axis of toroidal lamp 42. The exact value of the angle between the ellipse axis and the main axis of lamp 42 depends on the Numerical Aperture (NA) of the optical fiber. The toroidal flash tube is positioned so that its minor axis coincides with the focus of the ellipse. The other focus of the ellipse is at the edge of optical fiber 46. Reflector 44 may be machined from metal with the inner surfaces polished for good reflectivity. Aluminum is a very good reflector with high reflectivity in the visible and ultraviolet, and it may be used for this purpose. The reflector can be machined in one piece and then cut along a surface perpendicular to the main axis of the device. This will enable integration of the toroidal flash tube into the device.

Figure 4:
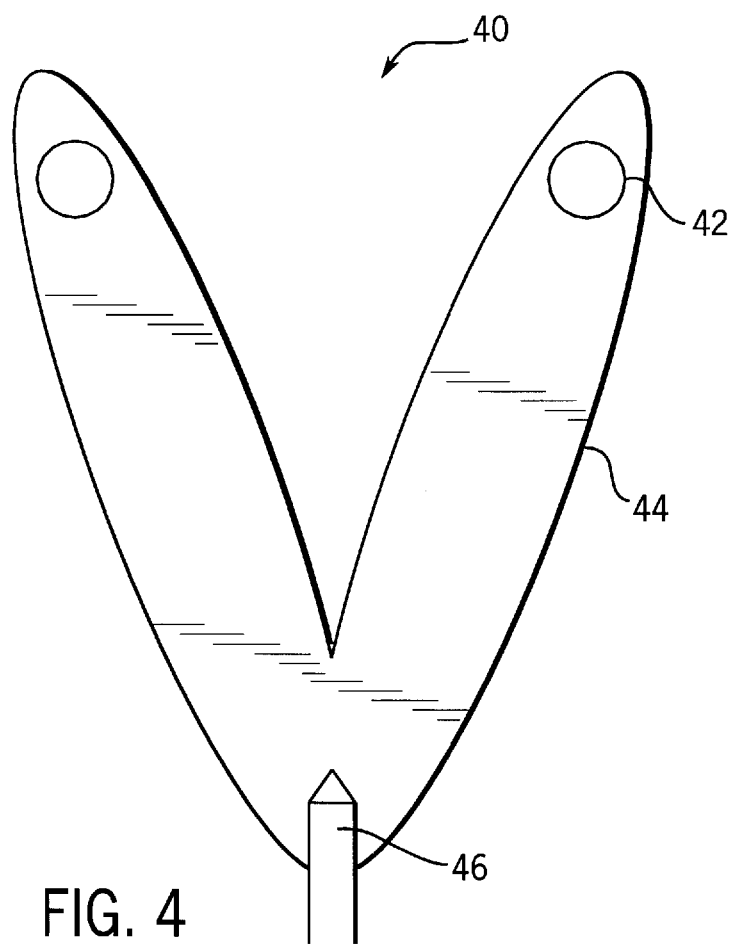
FIG. 4 is a cross-sectional view of a coupler for coupling light from a toroidal flash tube into an optical fiber with a conical edge.
Figure 7:
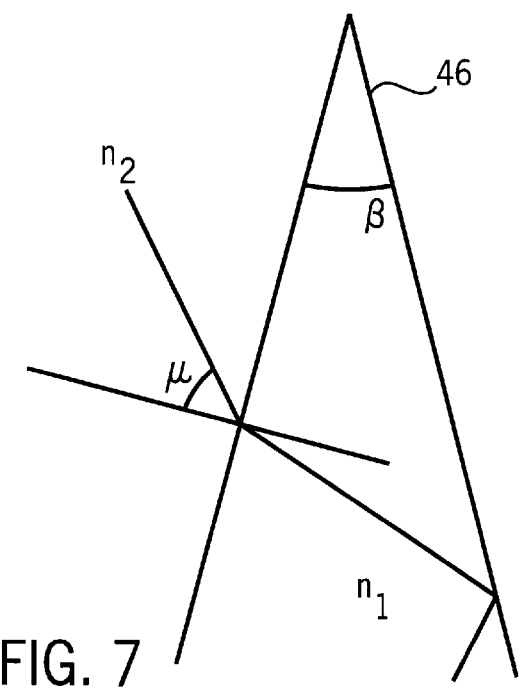
FIG. 7 shows the geometry for coupling into a conical section.

As shown in FIG. 4, the edge of optical fiber 46 is a cone with a small opening angle, so that the total area of the fiber exposed to the light from the flash tube is increased. Referring now to FIG. 7 the geometry for coupling light into a conical tip is shown. It is assumed here that the light comes from a region in space with a refractive index of $n_2$ and that the conical section of the fiber (as well as the rest of the fiber core) has a refractive index of $n_1$.

Not all the light rays hitting the cone are trapped in it. For light rays that propagate in a plane that contains the major axis of the system, a condition can be derived for the angle of a ray that will be trapped and absorbed in the fiber. This condition is shown in Equation 3.

$$\text{Sin }(\mu_{criti}) = \text{Cos }(\beta) - [n_1^2/n_2^2 - 1]^{1/2} \sin(\beta) \qquad \text{(Eq. 3)}$$

Light will be trapped in the conical portion of the optical fiber if the incidence angle $\mu$ is larger than $\mu_{criti}$ calculated from Equation 3. Trapping is possible only if $n_1 > n_2$. If the medium outside of the fiber is air, $n_2=1$. Not all of the light trapped in the conical section of the fiber will also be trapped in the straight portion of the fiber if a fiber with a core and a cladding is used. If a fiber with a core and no cladding is used (air cladding), then all the rays captured in the conical section of the fiber will also be trapped in the straight section of the fiber.

The configuration shown in FIG. 4 can also be used with a fluid filling the volume between the reflector and the optical fiber. A very convenient fluid for this purpose may be water. Water is also very effective in cooling the flashlamp if high repetition rate pulses are used. The presence of a fluid reduces the losses that are associated with glass to air transitions, such as the transition between the flashlamp envelope material and air. If a fluid is used in the reflector volume, then its refractive index can be chosen such that all the rays trapped in the conical section are also trapped in the fiber, even if core/cladding fibers are used.

Figure 8:
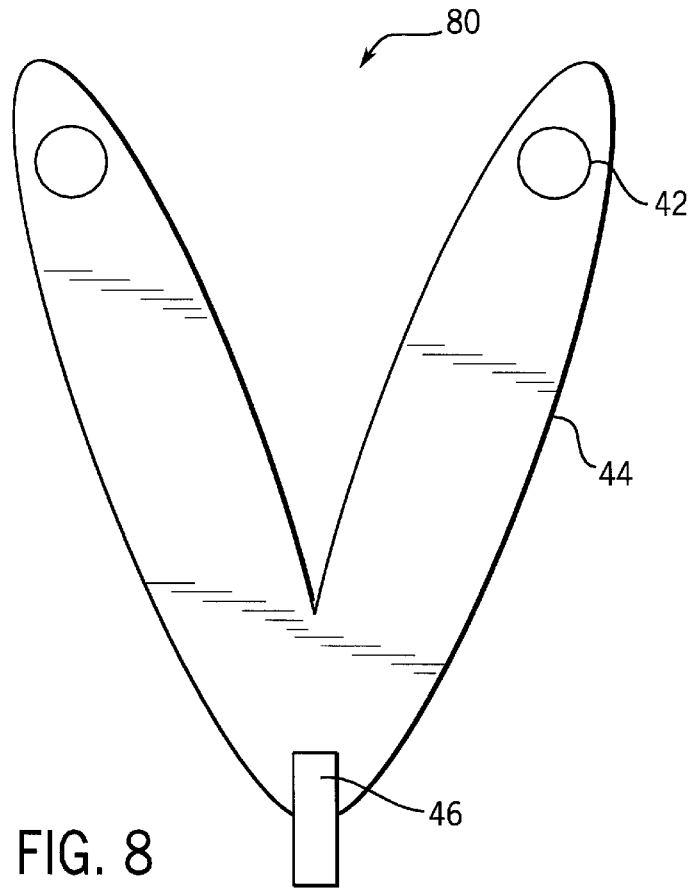
FIG. 8 is a cross-sectional view of a coupler for coupling light from a toroidal flash tube into an optical fiber with a flat edge.

Another way of configuring the fiber in the reflector is by using a fiber with a flat edge. This configuration is shown in FIG. 8 and has trapping efficiency very close to the trapping efficiency of the conical edge. Many other shapes of the fiber edge, such as spherical shapes, can also be used. The configuration of the fiber edge also has an effect on the distribution of the light on the exit side of the fiber and it can be chosen in accordance with the specific application of the device.

The device may be used with a variety of optical fibers. Single, or a small number of millimeter or sub-millimeter diameter fibers, will typically be used in invasive medical applications. In other applications, particularly in industrial and domestic applications, it may be preferable to use a fiber having a larger diameter, or a larger bundle of fibers, or a light guide.

Figure 9:
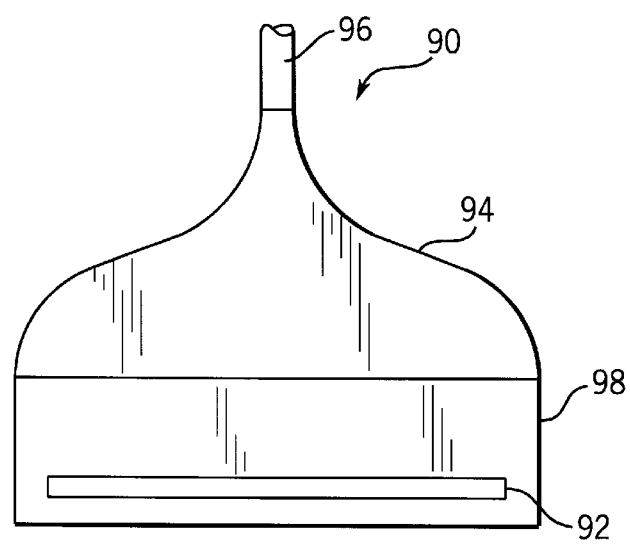
FIG. 9 is a front sectional view of a coupler for coupling light from a linear flash tube into a circular fiber bundle.
Figure 10:
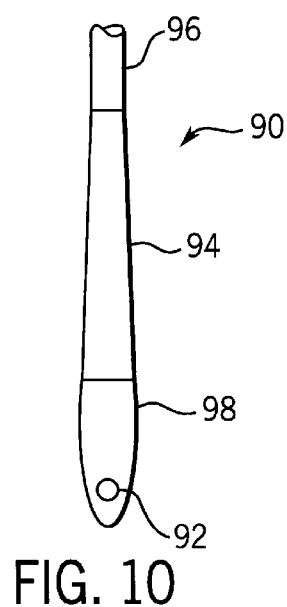
FIG. 10 is a side sectional view of the coupler of FIG. 9.

FIGS. 9 and 10 show a coupler 90 for coupling a linear flash tube 92 through a linear to circular fiber transfer unit 94 to a fiber bundle 96. A reflector 98 has an elliptical cross-section, shown in FIG. 10, in a plane parallel to the axis of linear flash tube 92 in this embodiment. Tube 92 is located on one focus of the ellipse while the linear side of linear to circular bundle converter 94 is located at the other focus of the ellipse. This configuration is relatively simple to manufacture and commercially available linear to circular converters such as 25-004-4 available from General Fiber Optics may be used. This configuration is particularly useful for larger exposure areas of the fiber, or for flash illumination purposes.

The energy and power densities that can be achieved by this invention are high enough to get the desired effects in surface treatment or medical applications. For the embodiment shown in FIG. 4 the total energy and power densities can be estimated as follows. For a typical toroidal lamp with a 4 mm bore diameter and a major diameter of 3.3 cm an electrical linear energy density input of 10 J/cm into the lamp can be used with a 5 $\mu$sec pulse width. The light output of the lamp will be 5 to 6 J/cm for optimal electrical operating conditions. For the reflector shown in FIG. 4, 50% of the light generated in the lamp will reach the lower focus. Thus, a total energy flux on the focus of 25 to 30 J may be obtained. For embodiments shown in FIG. 4 or FIG. 8 the total cross-section area of reflector at the focal plane has a cross-section of 0.8 cm$^2$. Energy densities on the order of 30 to 40 J/cm$^2$ at the entrance to the fiber should be attained with this cross-section. This corresponds to power densities of 5 to 10 MW/cm$^2$, which are the typical power densities used in medical or material processing applications.

For longer pulses, higher linear electrical energy densities into the lamp can be used. For a 1 msec pulse to the flash tube a linear electrical energy density of 100 J/cm can be used. The corresponding energy density at the focal area would be up to 300 J/cm$^2$. Such energy densities are very effective in industrial cleaning and processing applications as well as in medical applications.

Figure 11:
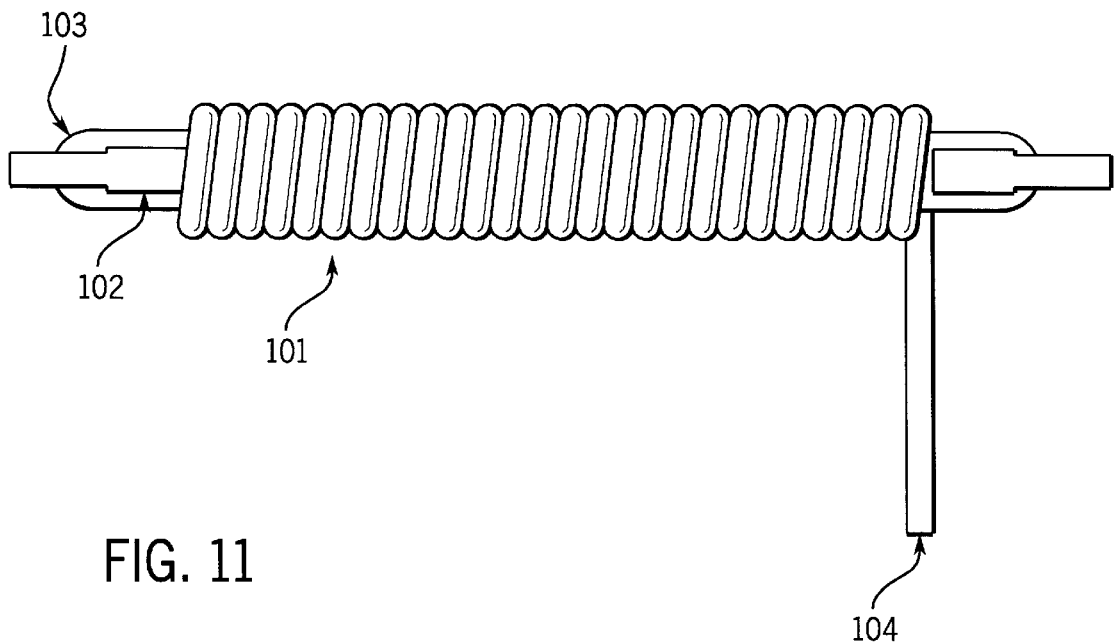
FIG. 11 is a front view of a coupler for coupling light from a linear flash tube into an optical fiber.
Figure 12:
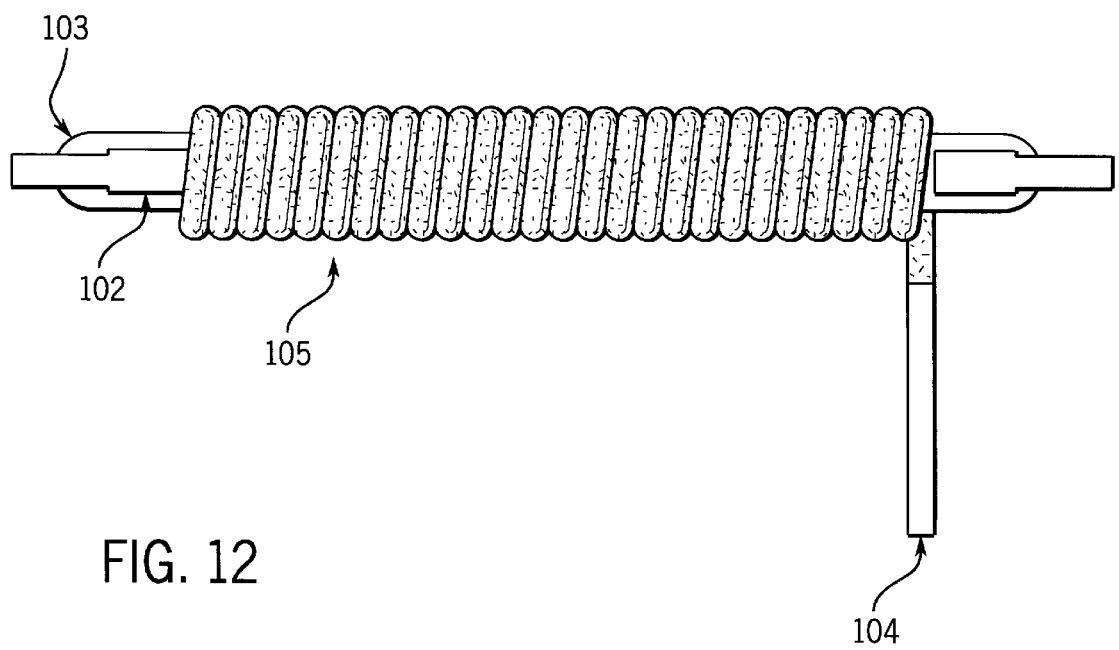
FIG. 12 is a front view of a coupler for coupling light from a linear flash tube into a doped optical fiber.

Alternative embodiments for coupling the optical fiber to an extended light source such as a linear flashlamp are shown in FIGS. 11 and 12. In the embodiment of FIG. 11 an optical fiber 101 is wound around a lamp 102 and a lamp envelope 103. Some of the light that is produced by the light source is coupled into the fiber. If the light rays are propagating in the direction that is trapped by the fiber then this light will propagate in the fiber and it can be used at a fiber output 104. One limitation of this configuration is the fact that most of the light emitted by lamp 103 travels in a direction perpendicular to the surface of lamp 103 and cannot be trapped in fiber 101.

The embodiment shown in FIG. 12 overcomes this problem. A doped optical fiber 105 is wound around lamp 102 and envelope 103, rather than an undoped fiber such as fiber 101 of FIG. 11. The dopant is a fluorescent material which is excited by the radiation emanating from lamp 102 and radiates light inside the fiber. This light is radiated omnidirectionally and the part of it that is within the critical angle of fiber 105 is trapped and propagates through the fiber and can be used at fiber output 104. The angle of light that is trapped in the fiber is the critical angle of the material from which the optical fiber or optical wave guide is made. For a fiber (or optical wave guide) in air this angle is given by sin α=1/n.

Typically for glass or other transparent materials n=1.5 and α=41.8°. This corresponds to a trapping efficiency of more than 10% of the light emitted by fluorescence inside the fiber. If we assume a 50% efficiency of the fluorescence process we find out that more than 5% of the light produced by the lamp is trapped and propagated down the fiber. For example, a 4" lamp with a linear electrical energy input of 300 J/inch and 50% electrical to light conversion efficiency would couple 2.5% of its electrical energy into the fiber. This corresponds, for the 4" lamp case to a total light energy of 30 J of light. This embodiment has the additional advantage of transferring the wavelength emitted by the lamp to a wavelength that may be more useful in some of the therapeutic or processing applications mentioned before. Thus, fluorescent material doped in the fiber can be chosen in accordance with an emission wavelength determined by the specific application of the device.

Thus, it should be apparent that there has been provided in accordance with the present invention a flashlamp and coupler that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

I claim:

1. A system of providing pulsed light comprising:

a pulsed toroidal flash tube incoherent light source having a spectrum of frequencies continuous over at least one bandwidth;

a reflector disposed about said incoherent light source, said reflector having a cross-section of substantially an ellipse, in a plane perpendicular to the minor axis of the toroidal light source; and at least one optical fiber having an end disposed within the reflector, the end of the optical fiber has a cone shape, wherein the cone shape of the end of the optical fiber opens away from the light source and wherein the cone shape of the end of the optical fiber has an included angle $\beta$, and a media outside the optical fiber has a refractive index of $n_1$, and the optical fiber has a refractive index of $n_2$, and $n_1 > n_2$, and an incidence angle of radiation which impinges upon the cone shape is $\mu$, and $\mu$ is less than $\mu_{criti}$ as defined in the equation:

$$\sin(\mu_{criti}) = \cos(\beta) - \{n_1^2/n_2^2 - 1\}^{1/2} \sin(\beta).$$

2. The system of claim 1, wherein the media outside the fiber is air.

3. The system of claim 2, wherein the optical fiber is a non clad fiber.

4. The system of claim 1, wherein the media outside the fiber is water.

* * * * *